United States Patent [19]

Gallagher

[11] Patent Number: 5,366,960
[45] Date of Patent: Nov. 22, 1994

US005366960A

[54] METHOD OF TREATING CEREBRAL AND CARDIOVASCULAR DISORDERS EMPLOYING [R]3-(2-DEOXY-β-D-ERYTHRO-PENTOFURANOSYL)-3,6,7,8-TETRAHYDROIMIDAZ 0-[4,5-D][1,3]DIAZEPIN-8-OL

[75] Inventor: Kim Gallagher, Ann Arbor, Mich.

[73] Assignee: Warner-Lambert Company, Morris Plains, N.J.

[21] Appl. No.: 112,746

[22] Filed: Aug. 26, 1993

[51] Int. Cl.$^5$ ............................................. A61K 31/70
[52] U.S. Cl. ........................................ 514/43; 514/46; 514/45; 536/27.13
[58] Field of Search ........................... 514/45, 46, 43; 536/22.13

[56] References Cited

U.S. PATENT DOCUMENTS

| | | | |
|---|---|---|---|
| 4,151,347 | 4/1979 | Umezawa et al. | 536/27.13 |
| 4,364,922 | 12/1982 | Berne et al. | 514/46 |
| 4,575,498 | 3/1986 | Holmes et al. | 514/43 |
| 4,673,563 | 6/1987 | Berne et al. | 514/46 |
| 4,713,372 | 12/1987 | Schaumberg et al. | 514/45 |
| 4,912,092 | 3/1990 | Gruber | 514/45 |
| 4,935,505 | 6/1990 | Townsend et al. | 536/27.13 |
| 5,104,859 | 4/1992 | Sollevi | 514/46 |
| 5,231,086 | 7/1993 | Sollevi | 514/46 |

FOREIGN PATENT DOCUMENTS 8705807  10/1987  WIPO .................... 514/43

OTHER PUBLICATIONS

Takahashi, "Albuminuria Improving Drug Contains 2'-Deoxy-coformycin", *Japanese Patent document SN 2,062,891*, Mar. 2, 1990; Derwent Abstract, 90-111969/15; only Abstract provided.

Boehringer Mannheim GmbH, "Imidazole-Ribosylcyclophosphates-(AICAR-3':5'-Cyclo-or-Monophosphates) with Antilipolytic Activity", *W. German Patent document SN 2,026,040*, Dec. 9, 1971; Derwent Abstract, 79007S-B; only Abstract supplied.

Swain et al., "Accelerated Repletion of ATP and GTP Pools in Postischemic Canine Myocardium Using a Precursor of Purine de Novo Synthesis", *Circulation*, 51(1), 102–105 (1982).

Mitsos et al., "Protective Effects of AICAriboside in the Globally Ischemic Isolated Car Heart", *Pharmacology*, 31, 121–131 (1985).

Bolling et al., "Augmenting Intracellular Adenosine Improves Myocardial Recovery", *J. Thorac. Cardiovasc. Surg.*, 99, 469–474 (1990).

Fukunaga et al., "Hypotensive Effects of Adenosine and Adenosine Triphosphate Compared with Sodium Nitroprusside", *Anesthesia and Analgesia*, 61(3), 273–278 (1982).

Hall et al., "Antiviral Drug and Interferon Combinations", Ch.3 in *Antiviral Agents: The Development and Assessment of Antiviral Chemotherapy*, vol. II, CRC Press, Boca Raton, Fla., 1987, pp. 29–43 and 74–77, note particularly Fig. 6 on p. 42.

Berkow et al. (eds.), *The Merck Manual of Diagnosis and Therapy*, 16th Ed., Merck Res. Labs., Rahway, N.J., 1992, see pp. 1450–1457.

(List continued on next page.)

Primary Examiner—John W. Rollins
Assistant Examiner—L. Eric Crane
Attorney, Agent, or Firm—Michael J. Atkins; Charles W. Ashbrook

[57] ABSTRACT

The present invention discloses the use of [R]-3-(2-deoxy-β-D-erythropentofuranosyl)-3,6,7,8-tetrahydroimidazo-[4,5-d][1,3]diazepin-8-ol, also commonly known as pentostatin, or a pharmaceutically acceptable salt thereof, or a pharmaceutical composition comprised of such compounds, in the prophylactic or affirmative treatment of cerebral and cardiovascular disorders such as cerebral and myocardial ischemia. The invention also discloses the administration of pentostatin along with adenosine in the prophylactic or affirmative treatment of cerebral and cardiovascular disorders.

9 Claims, 2 Drawing Sheets

OTHER PUBLICATIONS

Drury et al., "The Physiological Activity of Adenine Compounds with Especial Reference to Their Action Upon the Mammalian Heart", *J. Physiology (Cambridge)*, 68, 213–237 (1929).

Dawicki et al. (I), "Potentiation of the Antiplatelet Action of Adenosine in Whole Blood by Dipyridamole or Dilazep and the cAMP Phosphodiesterase Inhibitor, RA 233", *Thromb. Res.*, 43(2), 161–175 (1986); *Chem. Abstr.*, 105(7), p. 44, Abstr. No. 54382f (1984); only Abstract provided.

Goday et al., "Importance of Platelet-free Preparations for Evaluating Lymphocyte Nucleotide Levels in Inherited or Acquired Immunodeficiency Syndromes", *Clin. Sci.*, 65(6), 635–643 (1983); *Chem. Abstr.*, 100(1), p. 264, Abstr. No. 3045n (1984); only Abstract provided.

Hostetter et al., "The Erythrocyte as Instigator of Inflammation, Generation of Amidated C3 by Erythrocyte Adenosine Deaminase", *J. Clin. Invest.*, 84, 665–671 (1989).

Dawicki et al.(II), "Role of Adenosine Uptake and Metabolism by Blood Cells in the Antiplatelet Actions of Dipyridamole, Dilazep and Nitrobenzylthioinosine", *Biochemical Pharmacology*, 34(22), 3965–3972 (1985).

Masters et al., "Platelet Anti-aggregating and Hemodynamic Effects of Adenosine and Prostaglandin $E_1$", *Thorac. Cardiovasc. Surgeon*, 30, 14–20 (1982).

METHOD OF TREATING CEREBRAL AND CARDIOVASCULAR DISORDERS EMPLOYING [R]3-(2-DEOXY-β-D-ERYTHRO-PENTOFURANOSYL)-3,6,7,8-TETRAHYDROIMIDAZO-[4,5-D][1,3]DIAZEPIN-8-OL

FIELD OF THE INVENTION

The present invention concerns the use of [R]-3-(2-deoxy-β-D-erythropentofuranosyl)-3,6,7,8-tetrahydroimidazo[4,5-d][1,3]diazepin-8-ol (also commonly known as 2'-deoxycoformycin or pentostatin), or a pharmaceutically acceptable salt thereof for the prophylactic and affirmative treatment of cerebral and cardiovascular disorders, such as myocardial and cerebral ischemia.

More particularly, the present invention relates to methods for prophylactically and affirmatively treating various bodily states that respond beneficially to increases in extracellular levels of adenosine. In one embodiment, pentostatin is administered prophylactically or affirmatively as a single-agent treatment to patients undergoing coronary artery bypass grafting for the prevention of peri- and post-operative cardiac and cerebral ischemia events. In another embodiment, pentostatin is administered prophylactically or affirmatively along with adenosine to patients undergoing coronary artery bypass grafting for the prevention of peri- and post-operative cardiac and cerebral ischemia events.

BACKGROUND OF THE INVENTION

Approximately 400,000 coronary artery bypass graft (CABG) procedures are conducted annually in the United States. The frequency of the most debilitating problems (such as myocardial infarction, postoperative low cardiac output syndrome, and stroke) are estimated to be in the range of 5-10%, whereas modest cardiac dysfunction and cognitive disorders may have frequencies of 50-60%. Unfortunately it is difficult to obtain a precise fix on the frequency of heart and CNS related complications in surgeries with cardiopulmonary bypass because the definitions of "complications" vary and there may be a tendency to miss significant problems when they are assessed retrospectively rather than observed prospectively. Even if estimates as low as 5% are correct, this percentage represents 20,000 patients that will be able to benefit from improved protection during a CABG operation. A potentially more important factor that could influence the complication rates now and in the future may be the changing demographics of the surgical populations. Since patients undergoing CABG procedures are tending to be older and higher risk individuals as the general population ages, it appears likely that the frequency of serious complications will increase.

During CAGB operations, the heart and lungs are isolated from the rest of the circulatory system which is supported by a cardiopulmonary bypass pump. Hypothermia, cardioplegia and other means of protecting the heart or brain are used routinely in CABG procedures, but ischemia remains a significant and serious risk that can lead to myocardial infarction, prolonged postoperative dysfunction, stroke, or cognitive disorders.

Adenosine receptor activation is an important part of ischemic events. Swain et al., *Circulation Research*, 1982, 51:102-105; Holmes et al., U.S. Pat. No. 4,575,498 (issued Mar. 11, 1986); and Mitsos et al., *Pharmacology*, 1985, 31:121-131. Techniques that would increase extracellular levels of adenosine or adenosine analogs at specific times during a pathological event such as ischemia, that would increase these compounds without complex side effects, would therefore be of considerable therapeutic use. One reason for lower levels of adenosine has to do with the presence of the enzyme, adenosine deaminase, in the ischemic area.

Several methods exist for increasing the activation of adenosine receptors. One method is the systemic administration of adenosine. Unfortunately, the systemic administration of adenosine or adenosine analogs tends to reduce blood pressure and induce bradycardia. Therefore, another mechanism of increasing adenosine levels only in the ischemic area is necessary, this would permit increased adenosine levels to be selectively targeted to cells that would benefit most from them.

One alternate mechanism for increasing adenosine levels is to inhibit adenosine deaminase. U.S. Pat. No. 4,912,092 issued Mar. 27, 1990 to Gruber discloses methods for increasing extracellular concentrations of adenosine for the prophylactic or affirmative treatment of diseases of the cardiac and vascular systems involving administering to a patient purine nucleoside and purine nucleoside-related analogs which increase extracellular adenosine concentration. Examples of compounds useful in the invention include compounds broadly classified as purine nucleosides and related analogs, such as AICA riboside, in various pro-forms. The Gruber reference also discloses that pentostatin is a potent inhibitor of the enzyme adenosine deaminase that enhances the effect of the purine nucleoside in elevating adenosine concentrations for a bodily condition. One of the bodily conditions the compounds may be administered to include seizure activity, arrhythmias, or a condition resulting in decreased blood flow. The disclosure of the Gruber reference is hereby incorporated by reference.

World Patent Application 87/05807 to H. E. Gruber, claims a method of treating an animal body for diseases associated with restricted blood flow comprising the administration of purine nucleosides, which may be AICA riboside. The application also claims the use of 2'-deoxycoformycin to enhance the effect of said purine nucleosides. The application is related to U.S. Pat. No. 4,912,092 issued to H. E. Gruber on Mar. 27, 1990 which is discussed above.

U.S. Pat. No. 4,713,372 issued Dec. 15, 1987 to Schaumberg discloses the administration of pentostatin to inhibit adenosine deaminase in order to combat viruses. The patent does not disclose the use of pentostatin to prophylactically or affirmatively treat cerebral and cardiovascular disorders.

The literature contains reports on the effects of adenosine deaminase inhibitors which were used to enhance or maintain local adenosine levels in the heart and brain. For example, pentostatin and erythro-9 (2-hydroxy-3-nonyl) adenine (EHNA) improved functional and metabolic recovery after global ischemia in isolated rabbit (Bolling SF, Bies LE, Bore El, Gallagher KP, Augmenting intracellular adenosine improves myocardial recovery, *J Thorac Cardiovasc Surg* 99: 469-474, 1990) and rat hearts (Dhasmana JP, Digerness SB, Geckle JM, Ng TC, Glickson JD, Blackstone EH: Effect of adenosine deaminase inhibitors on the heart's functional and biochemical recovery from ischemia: A study utilizing the isolated rat heart adapted to 31-P nuclear magnetic resonance. *J Cardiovasc Pharm* 5: 1040-1047, 1983). In the brain, inhibition of adenosine deaminase lead to accumulation of interstitial adenosine in rats (Sciotti VM, Van Wylen DGL: Increases in interstitial adenosine and cerebral blood flow with inhibition of adenosine kinase and adenosine deaminase. *J Cereb Blood Flow Metab* 13: 201–207, 1993) and pentostatin (0.5 mg/kg, corresponding approximately to 3.0 mg/m$^2$ in humans) has been demonstrated to have beneficial effects in rat and gerbil models of cerebral ischemia or hypoxia (Phillis JW, O'Regan MH, Walter GA: Effects of deoxycoformycin on adenosine, inosine, hypoxanthine, xanthine, and uric acid release from the hypoxemic rat cerebral cortex. *J Cereb Blood Flow Metab* 8: 733–741, 1988; Phillis JW, O'Regan MH: Deoxycoformycin antagonizes ischemia-induced neuronal degeneration. *Brain Res Bull* 22: 537–540, 1989; Phillis JW, Walter GA, Simpson RE: Brain adenosine and transmitter amino acid release from the ischemic rat cerebral cortex: Effects of the adenosine deaminase inhibitor deoxycoformycin. *J Neurochem* 56: 644–650, 1991). In one report, however, in rat model of transient forebrain ischemia, no beneficial effects of pentostatin were observed (Delaney SM, Sutherland GR, Peeling J, Geiger JD: Failure of 2'-deoxycoformycin to protect against transient forebrain ischemia in rat. *Neuroscience Letters* 149: 31–34, 1993).

[R]-3-(2-deoxy-β-D-erythropentofuranosyl)-3,6,7,8-tetrahydroimidazo[4,5-d][1,3]diazepin-8-ol, 2'-deoxycoformycin or pentostatin, is described in U.S. Pat. No. 3,923,785. The compound is disclosed there as having in vitro and in vivo activity against DNA viruses such as herpes and vaccinia. A method for purifying pentostatin is disclosed in copending U.S. application Ser. No. 07/738,715 filed Jul. 31, 1991. The patent and patent application are hereby incorporated by reference.

There is no disclosure in the above references to suggest the methods of the present invention for increasing extracellular adenosine concentration to allow adenosine receptor activation in ischemic areas, thus treating cerebral and cardiovascular disorders such as myocardial and cerebral ischemia.

SUMMARY OF THE INVENTION

Accordingly, the present invention provides a method for treating cerebral and cardiovascular disorders which comprises prophylactically or affirmatively administering to a patient in need thereof an effective amount of a compound as a single-agent having the Formula I

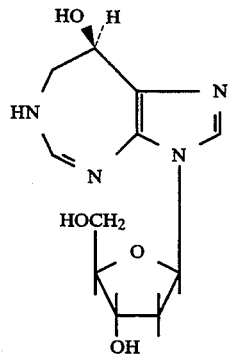

The present invention also includes a method for treating cerebral and cardiovascular disorders which comprises prophylactically or affirmatively administering to a patient in need thereof a therapeutically effective amount of a compound of Formula I together with a pharmaceutically acceptable carrier in unit dosage form.

The present invention also includes a method for treating cerebral and cardiovascular disorders which comprises prophylactically or affirmatively administering to a patient in need thereof a therapeutically effective amount of a compound of Formula I together with adenosine.

The present invention also includes a method for treating cerebral and cardiovascular disorders which comprises prophylactically or affirmatively administering to a patient in need thereof a therapeutically effective amount of a compound of Formula I together with adenosine and a pharmaceutically acceptable carrier in unit dosage form.

The invention also includes a method of treating cerebral ischemia, cerebral infarction, cerebral vasospasm, cardiac arrest, cerebral trauma, myocardial ischemia, myocardial infarction, peri-, intra-, and post-operative cardiac and cerebral ischemic events comprising prophylactically or affirmatively administering to a patient in need thereof a therapeutically effective amount of the above compositions.

The invention also includes a method of treating stroke or other event involving an undesired, restricted or decreased blood flow, such as atherosclerosis, in patients in need thereof which comprises prophylactically or affirmatively administering to a patient in need thereof a therapeutically effective amount of the above compositions.

DETAILED DESCRIPTION OF THE INVENTION

The present invention is directed to a method of prophylactically and affirmatively treating disease by increasing the excretion of cellular adenosine including diseases of the immune, nervous and vascular systems involving in one embodiment, prophylactically or affirmatively administering to a patient an inhibitor of adenosine deaminase, such as pentostatin, in order to increase the concentration of intracellular adenosine. In another embodiment, the present invention involves prophylactically or affirmatively administering to a patient an inhibitor of adenosine deaminase, such as pentostatin, along with the administration of adenosine, in order to increase the concentration of intracellular adenosine.

In a preferred embodiment of the present invention, the inventor has developed the approach that ischemic preconditioning will modify myocardial ischemic tolerance. This phenomenon reduces infarct size more drastically than most pharmacologic agents. The myocardium is stressed with a brief episode of ischemia, reperfused for a few minutes, and then exposed to a longer period of ischemia. Preconditioning can reduce infaract size by 75% or so, as long as the ischemic episode is not too long and the reperfusion period is kept relatively short.

Figure 1:
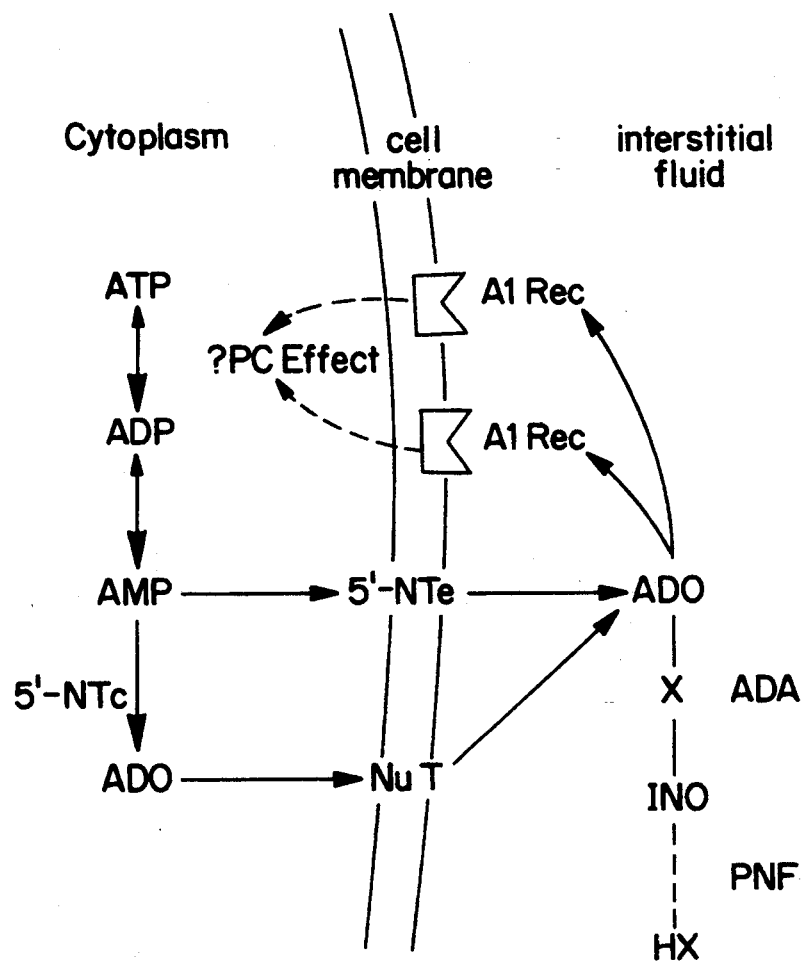
FIG. 1 is a scheme of events to explain hypothetical effects of pentostatin during ischemia.

Whereas the inventor does not wish to be bound by theory, the rationale for using pentostatin to protect the heart (FIG. 1) and brain is based on the principle that adenosine can modify and minimize the effects of ischemia. Delivery of exogenous adenosine, however, is complicated by the filtering effects of the endothelium and can produce deleterious consequences such as hypotension, bradycardia, and A-V dissociation. Since ischemic tissue itself represents a potential source of adenosine, the present invention takes advantage of it by inhibiting its metabolism to inosine by adenosine deaminase. Pentostatin could minimize the consequences of ischemia by augmenting locally produced adenosine within an ischemic area (site specificity) during ischemic episodes (condition specificity).

Augmentation of the locally produced adenosine occurs because pentostatin is an inhibitor of the enzyme, adenosine deaminase. Normally, adenosine is broken down rapidly because of adenosine deaminase. Pentostatin keeps adenosine levels high in ischemic myocardium by inhibiting adenosine deaminase.

Although a substantial number of mechanisms have been identified to explain the beneficial effects of adenosine in ischemia, the present invention is based on recent studies linking activation of adenosine A1 receptors to initiation and maintenance of the preconditioning effect (Downey JM, Liu GS, Thornton JD: Adenosine and the anti-infarct effects of preconditioning. *Cardiovasc Res* 27: 3–8, 1993; Mullane K: Myocardial preconditioning. Part of the adenosine revival. *Circulation* 85: 845–847, 1992). Preconditioning refers to the phenomenon whereby brief episodes of ischemia induce striking myocardial protection, measured as infarct size reduction after subsequent, prolonged coronary occlusions (Murry CE, Jennings RB, Reimer KA: Preconditioning with ischemia: a delay of lethal cell injury in ischemic myocardium. *Circulation* 74: 1124–1135, 1986). Clinical evidence suggests that preconditioning occurs in human patients (Deutsch E, Berger M, Kussmaul WG, Hirshfeld JW, Herrmann HC, Laskey WK: Adaptation to ischemia during percutaneous transluminal coronary angioplasty. *Circulation* 82: 2044–2051, 1990), as well as experimental animals. The inventor postulates that pentostatin, by inhibiting adenosine deaminase, will augment and sustain accumulation of adenosine in the interstitium around ischemic cells improving their ability to tolerate ischemic episodes similar to the preconditioning effect.

Figure 2:
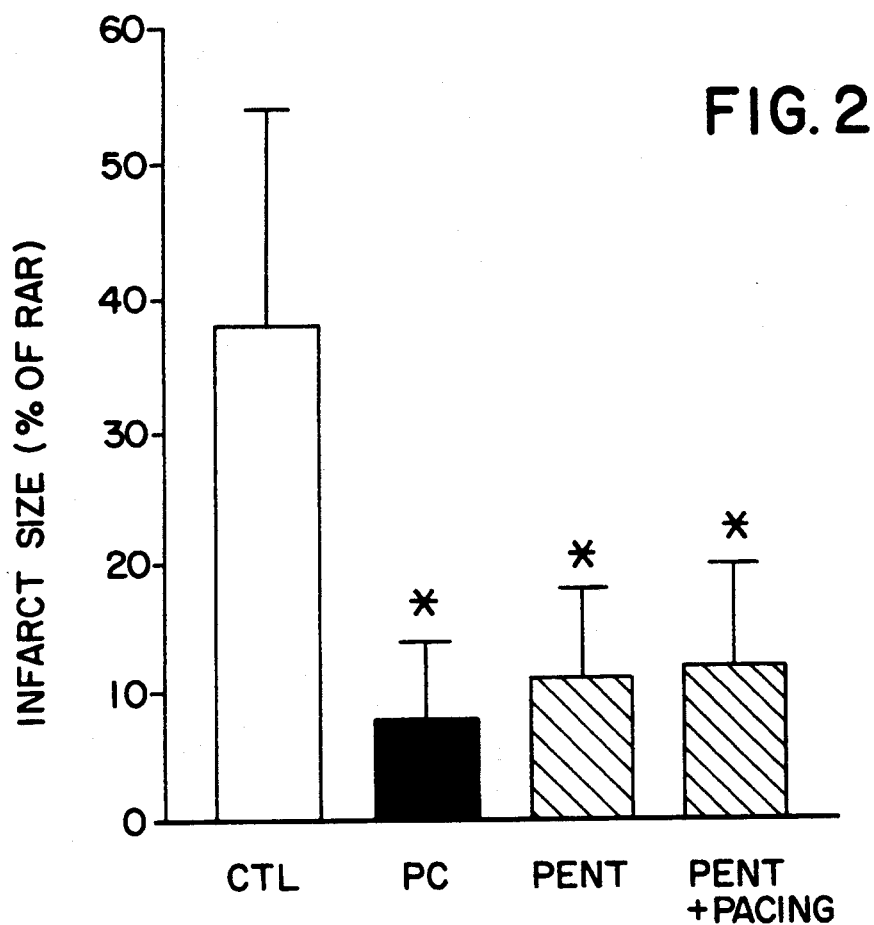
FIG. 2 is a graph representing the infarct size of test subjects in Example 1.

The hypothesis to explain the potential beneficial actions of pentostatin during ischemia is summarized in simplified form in FIG. 2. During normal conditions, tissue adenosine levels are very low as nearly all of the adenosine is phosphorylated in the form of adenine nucleotides. During ischemia, high energy phosphate compounds are consumed and cannot be repleted leading to elevations of local adenosine levels. The extent to which adenosine levels can increase is limited in part by adenosine deaminase which metabolizes adenosine to inosine. Inhibition of adenosine deaminase with pentostatin should augment local adenosine levels, a contention supported by experimental measurements of whole tissue (Bolling SF et al., supra) and interstitial adenosine levels with adenosine deaminase inhibition (Dorheim TA, Hoffman A, Van Wylen DGL, Mentzer RM, Jr: Enhanced interstitial fluid adenosine attenuates myocardial stunning. *Surgery* 110: 136–145, 1991; Wang T, Mentzer RM, Jr, Van Wylen DGL: Coronary blood flow and interstitial adenosine with dipyridamole: effect of adenosine receptor blockade and adenosine deaminase. *Am J Physiol* 263: H552–H558, 1992). The elevated interstitial levels of adenosine, in turn, can occupy adenosine A1 receptors on the outer surface of the cell membrane, potentially activating the signal transduction pathways that culminate in preconditioning or preconditioning-like enhancement of ischemic tolerance. Thus, the cytoprotection conferred by elevated adenosine levels may minimize the extent and complications of ischemia in the heart and brain, a direct benefit for the patient that may also reduce overall medical costs by reducing time to hospital discharge.

Whereas it is known in the art that pentostatin may be administered as a reagent with purine nucleosides and related analogs, such as AICA riboside, the inventor of the present invention has discovered that the single-agent administration of pentostatin to treat cerebral and cardiovascular disorders is beneficial. Single-agent administration of pentostatin has been shown to result in prophylactic or affirmative treatment of cerebral and cardiovascular disorders as the administration of pentostatin with purine nucleosides. In addition, single-agent administration of pentostatin may be administered in a single bolus rather than as a sustained infusion, therefore lower concentrations of pentostatin are administered. The administration of a low concentration of pentostatin also results in decreased toxicity.

In addition, whereas it is known in the art that the systemic administration of adenosine or adenosine analogs tends to reduce blood pressure and induce bradycardia, the inventor of the present invention has discovered that the single administration of the adenosine deaminase inhibitor, pentostatin, along with adenosine to treat cerebral and cardiovascular disorders is beneficial.

The term, "cerebral and cardiovascular disorders" is defined herein to mean cerebral ischemia, cerebral infarction, cerebral vasospasm, cardiac arrest, cerebral trauma, myocardial ischemia, myocardial infarction, peri-, intra-, and post-operative cardiac and cerebral ischemic events. The term ischemic events may be defined to include stroke or other events involving an undesired, restricted or decreased blood flow, such as atherosclerosis.

It should further be mentioned that the methods of the present invention may also be useful in the prophylactic and affirmative treatment of patients who have chronic low adenosine such as those suffering from autism, cerebral palsy, insomnia and other neuropsychiatric symptoms, including schizophrenia.

The compound of Formula I is useful for the treatment of cerebral and cardiovascular disorders such as myocardial and cerebral ischemia both in the free base form and in the form of acid addition salts. The two forms are within the scope of the present invention. Pharmaceutically acceptable acid addition salts are formed with inorganic and organic acids, such as, for example, hydrochloric, sulfuric, phosphoric, acetic, citric, gluconic, fumaric, methanesulfonic and the like (see, for example, Berge SM, et al., Pharmaceutical Salts, *Journal of Pharmaceutical Science* 66: 1–19, 1977). The acid addition salts of said basic compound are prepared by contacting the free base form with a sufficient amount of the desired acid to produce the salt in the conventional manner. The free base form may be regenerated by contacting the salt form with a base and isolating the free base in the conventional manner. The free base form differs from its respective salt forms somewhat in certain physical properties such as solubility in polar solvents, but otherwise the salts are equivalent to their respective free base for purposes of the present invention.

The compounds of the invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compound of the present invention, pharmaceutically acceptable carriers can be either solid or liquid. Solid form preparations include powders, tablets, pills, capsules, dispersible granules, cachets, and suppositories. A solid carrier can be one or more substances which may also act as diluents, flavoring agents, solubilizers, lubricants, suspending agents, binders, preservatives, tablet disintegrating agents or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool and thereby to solidify.

Liquid form preparations include solutions, suspensions, and emulsions, for example, water or water propylene glycol solutions.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet or lozenge itself or it can be the appropriate number of any of these in packaged form.

The compound of the present invention or one of its pharmaceutically acceptable salts is generally administered to the patient in need of treatment in the form of an intravenous formulation. Certain of the ester derivatives of the present invention may be administered in oral dosage form.

Sterile solutions of the compound of the present invention suitable for injection is formed by dissolving the compound or desired salt form in a sterile solvent and subsequently sealing the sterile solution in vials or ampoules. Alternatively, the solution can be prepared and then subsequently sterilized by passage through micropore filters for sterilization.

Suitable solvents for the preparation of sterile parenteral solutions include pyrogen-free sterile solvents containing water, ethanol, polyols (e.g., glycerol, propylene glycol, liquid polyethylene glycol, and the like), N,N-dimethylacetamide, suitable mixtures thereof, and sterile vegetable oils.

Sterile powders for the reconstitution as injectable formulations are prepared by vacuum or freeze-drying previously prepared sterile solutions.

Parenteral preparations may contain from 0.1 to about 500 mg/ml of active components, with 0.5 to about 250 mg/ml being preferred.

In use for treating cerebral and cardiovascular disorders, the particular dose employed of a composition comprising the compounds of the present invention is varied, depending upon a number of factors including the previous medical history and condition of the patient, the severity of the condition being treated, and the potency of the drug being administered. Determination of the appropriate dosage for a particular situation is within the skill of the art.

It should further be understood that the present invention is also directed to combinations of the compound of this invention or its pharmaceutical salts with one or more known agents known to be useful in the treatment of cerebral and cardiovascular disorders. For example, the compound of this invention may be effectively administered in combination with effective amounts of adenosine analogs or other adenosine deaminase inhibitors known to those of ordinary skill in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLE

Example 1

The inventor has evaluated pentostatin in myocardial ischemia. The initial studies were performed to determine the effects of pentostatin on infarct size in the anesthetized, open-chest rabbit. Although the rabbit infarct model is characterized by substantial variability, it has proven useful as a screening model to evaluate the potential anti-ischemic utility of various physiologic and pharmacologic interventions. In the first series of experiments with penetration, the rabbits were pretreated with 2.0 mg/kg or 0.02 mg/kg (corresponding approximately to 22.0 mg/m$^2$ and 0.22 mg/m$^2$ in humans) pentostatin 30 minutes before a 30 minute occlusion of a major coronary artery. Infarct size was approximately 40–50% smaller in the pentostatin pretreated animals compared to control animals.

To conduct a more detailed evaluation of pentostatin's potential in a large animal model, experiments were conducted in anesthetized, open-chest Micropigs undergoing 60 minutes of left anterior descending coronary occlusion followed by three hours of reperfusion. Anesthesia was maintained with the volatile agent isoflurane after induction with ketamine and lidocaine was continuously infused in all of the animals to minimize the development of intractable ventricular fibrillation. As shown in FIG. 2, infarct size in the control animals averaged approximately 38% of the region at risk (RAR). Pretreatment with 0.2 mg/kg (approximate human equivalent dose, 4.0 mg/m$^2$) pentostatin was associated with infarcts that averaged 11% (n=6) of the RAR. Because pentostatin in the pig reduced heart rate, a trial pacing was used in an additional six animals pretreated with the same dose of pentostatin. In this group, infarct size averaged 12% (n=6) of the RAR, similar to the unpaced animals pretreated with pentostatin suggesting that the effect of pentostatin on heart rate was not responsible for the reduction in infarct size.

The differences in infarct size could not be attributed to variations in the size of regions at risk which were not significantly different among the groups (averaging 20–25% of the left ventricle) or hemodynamics (except for heart rate in the unpaced pentostatin group). The remaining major determinant of infarct size, collateral perfusion during occlusion, was not a factor because the study was conducted in pigs, a species that consistently lacks significant native collateral investment. It is notable that the 70% reduction in infarct size associated with pentostatin in the pig was similar to the effect of preconditioning, which reduced infarct size to an average of 8% (n=8) of the RAR in this model.

Infarct modification studies address one important endpoint, development of irreversible injury. Another important endpoint relative to a cardiac surgical indication, however, is functional recovery of the left ventricle after ischemia. To pursue the effects of pentostatin on functional recovery, a study was contracted. The study was conducted in dogs on cardiopulmonary bypass. The experimental model represents a severe test of any intervention because the heart is exposed to 30 minutes of normothermic ischemia before hypothermic blood cardioplegia is delivered.

The protocol consisted of baseline measurements to define left ventricular function (utilizing arrays of sonomicrometers and high fidelity pressure transducers to enable calculation of preload recruitable stroke work), aortic crossclamping for a total of 90 minutes (30 minutes of normothermic, global ischemia followed by blood cardioplegia and 60 minutes of hypothermic ischemia), removal of the crossclamp, and weaning the heart from cardiopulmonary bypass support. When the heart is completely weaned, functional measurements are repeated to determine the extent to which the left ventricle has recovered.

Figure 3:
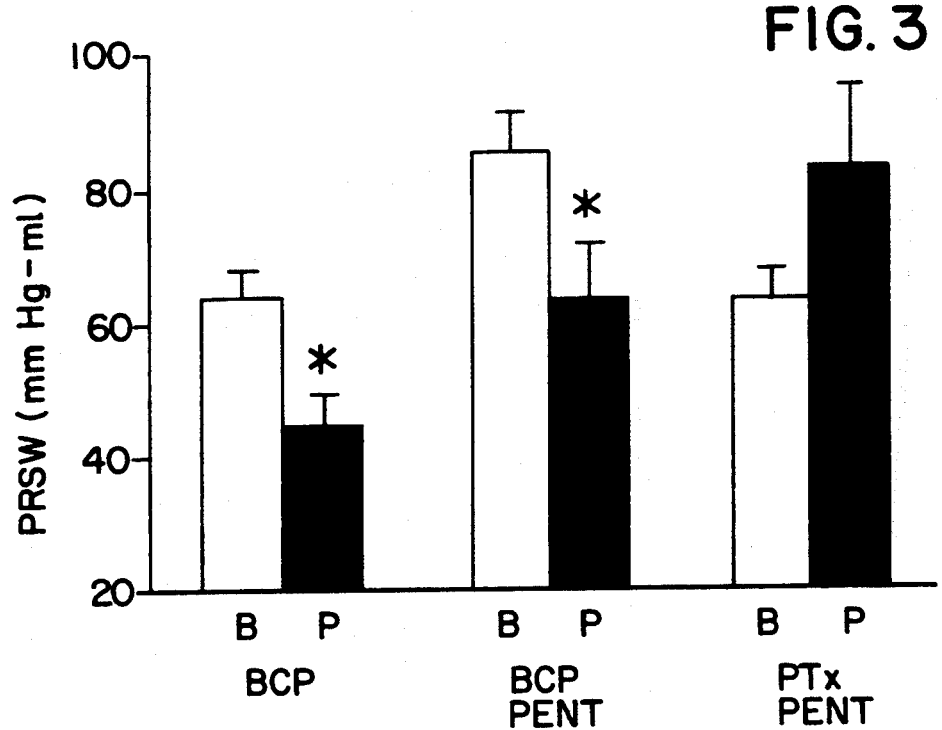
FIG. 3 is an index of left ventricular contractile performance in test subjects of Example 1.

As shown in FIG. 3, postischemic left ventricular performance (preload recruitable stroke work) was restored to baseline levels or greater in the pentostatin (0.2 mg/kg; approximate human equivalent dose 4.0 mg/m$^2$) pretreatment group (n=7) after weaning from cardiopulmonary bypass was completed. Left ventricular performance was significantly depressed, however, in the control blood cardioplegia (n=6) and pentostatin supplemented cardioplegia (n=6) groups.

In the control blood cardioplegia group, myocardial microdialysate adenosine (an index of interstitial adenosine levels) increased modestly during normothermic ischemia (from 0.5±0.1 μM) but was not augmented further after cardioplegia was administered. Similar results were obtained in the group that received cardioplegia supplemented with pentostatin. In the group pretreated with pentostatin, microdialysate adenosine levels increased to a greater extent during normothermic ischemia (from 0.6±0.2 μM to 37.8±17.1 μM) and remained elevated after cardioplegia was administered (40.3±17.9 μM). Thus, the data indicated that pretreatment with pentostatin augmented endogenous adenosine levels and reduced postischemic dysfunction in ischemically injured canine hearts.

I claim:

1. A method of reducing infarct formation in a mammal comprising administering to an individual in need thereof a therapeutically effective amount of a compound having the Formula I

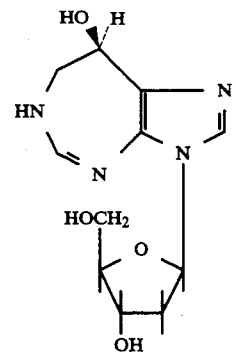

or a pharmaceutically acceptable acid addition salt thereof as the sole pharmaceutically active ingredient.

2. A method of claim 1 wherein the infarct reduction occurs in the brain.

3. A method of claim 1 wherein the compound is administered along with a pharmaceutically acceptable carrier.

4. The method of claim 1 wherein said compound of Formula I is administered parenterally, intravenously or enterally.

5. The method of claim 1 wherein said compound is administered to a patient in a single bolus.

6. A method of claim 1 wherein the infarct reduction occurs in the myocardium.

7. A method of claim 6 wherein the compound is administered along with a pharmaceutically acceptable carrier.

8. The method of claim 6 wherein said compound of Formula I is administered parenterally, intravenously or enterally.

9. The method of claim 6 wherein said compound is administered to a patient in a single bolus,

* * * * *